(12) United States Patent
Ono

(10) Patent No.: US 8,985,770 B2
(45) Date of Patent: Mar. 24, 2015

(54) OPHTHALMIC IMAGING APPARATUS, METHOD OF CONTROLLING OPTHALMIC APPARATUS AND STORAGE MEDIUM

(75) Inventor: Shigeaki Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 449 days.

(21) Appl. No.: 13/427,142

(22) Filed: Mar. 22, 2012

(65) Prior Publication Data
US 2012/0249953 A1 Oct. 4, 2012

(30) Foreign Application Priority Data
Mar. 31, 2011 (JP) .................. 2011-079801

(51) Int. Cl.
*A61B 3/14* (2006.01)
*A61B 3/00* (2006.01)
*A61B 3/10* (2006.01)

(52) U.S. Cl.
CPC ...................................... *A61B 3/102* (2013.01)
USPC ........... 351/206; 351/200; 351/205; 351/210; 351/221

(58) Field of Classification Search
CPC ............ A61B 3/14; A61B 3/12; A61B 3/103; A61B 3/113; A61B 3/1225; A61B 3/024; A61B 3/1015
USPC ......... 351/206, 200, 205, 209–210, 221–222, 351/246
See application file for complete search history.

(56) References Cited

U.S. PATENT DOCUMENTS

| | | | |
|---|---|---|---|
| 5,894,337 A | 4/1999 | Okinishi et al. | |
| 6,192,269 B1 | 2/2001 | Okumura et al. | |
| 6,332,683 B1 | 12/2001 | Ono et al. | |
| 6,337,993 B1 | 1/2002 | Kishida et al. | |
| 6,535,757 B2 | 3/2003 | Ono | |
| 6,569,104 B2 | 5/2003 | Ono et al. | |
| 6,834,202 B2 | 12/2004 | Ono | |
| 7,488,071 B2 | 2/2009 | Ogawa et al. | |
| 7,744,221 B2 | 6/2010 | Wei et al. | |
| 2008/0208525 A1* | 8/2008 | Kikawa et al. | 702/172 |
| 2010/0110171 A1 | 5/2010 | Satake | |
| 2012/0083667 A1* | 4/2012 | Isogai et al. | 600/300 |

FOREIGN PATENT DOCUMENTS

| | | |
|---|---|---|
| JP | 2008-142443 A | 6/2008 |
| JP | 2009-523563 A | 6/2009 |
| JP | 2010-110392 A | 5/2010 |
| JP | 2011-005236 A | 1/2011 |
| JP | 2011-095005 A | 5/2011 |
| WO | 20071084748 A2 | 7/2007 |

* cited by examiner

*Primary Examiner* — Dawayne A Pinkney
(74) *Attorney, Agent, or Firm* — Fitzpatrick, Cella, Harper & Scinto

(57) ABSTRACT

An ophthalmic imaging apparatus which obtains a tomographic image of an eye to be examined based on light obtained by combining return light from the eye irradiated with measurement light with reference light corresponding to the measurement light, the apparatus comprising: a scanning unit configured to scan the measurement light on the eye; and a control unit configured to control the number of times of scanning by the scanning unit in accordance with a scanning position of the scanning unit on the eye.

14 Claims, 9 Drawing Sheets

OPHTHALMIC IMAGING APPARATUS, METHOD OF CONTROLLING OPTHALMIC APPARATUS AND STORAGE MEDIUM

BACKGROUND OF THE INVENTION

1. Field of the Invention

The present invention relates to an ophthalmic imaging apparatus which images an eye to be examined, a method of controlling the ophthalmic imaging apparatus, and a storage medium.

2. Description of the Related Art

Currently, various types of ophthalmic apparatuses using optical apparatuses are used. For example, various types of apparatuses such as an anterior ocular segment imaging apparatus, fundus camera, and scanning laser ophthalmoscope (SLO) are used as optical apparatuses for observing the eyes. Of these apparatuses, an optical tomography apparatus based on optical coherence tomography (OCT) using multiwavelength interference is an apparatus capable of obtaining a tomographic image of a sample with a high resolution. This apparatus has been becoming indispensable as an ophthalmic apparatus for out-patient clinics dedicated to retinal diseases. This apparatus will be referred to as an OCT apparatus hereinafter.

An OCT apparatus can measure a slice of an object to be examined by splitting measurement light which is low-coherent light into reference light and measurement light, irradiating the object with the measurement light, and making return light from the object interfere with the reference light. The OCT apparatus can obtain a high-resolution tomographic image by scanning measurement light on a sample. This apparatus therefore obtains a tomographic image of the retina of the fundus of the eye to be examined, and is widely used for ophthalmic diagnosis of the retina. If, however, the object to be examined is a living organism like the eye, the distortion of an image due to the movement of the eye poses a problem. Demands have therefore risen for high-speed, high-sensitivity measurement.

Japanese Patent Laid-Open No. 2009-523563 has proposed an OCT apparatus which obtains OCT images corresponding to scan patterns used for scanning of a plurality of portions. A scan pattern consists of a plurality of concentric circles and a plurality of radial lines.

Japanese Patent Laid-Open No. 2010-110392 has proposed an OCT apparatus which performs addition processing of a plurality of tomographic images obtained by imaging the same region and averaging pixel values to reduce the influence of noise which occurs irregularly. At this time, the OCT apparatus segments a captured image into a plurality of regions, and detects positional shift information between the respective captured images for each segmented region. The apparatus then performs correction for each segmented region based on the positional shift information, and averages the respective corrected images.

Although the OCT apparatus disclosed in Japanese Patent Laid-Open No. 2009-523563 has a scan pattern for scanning a plurality of areas obtained by segmenting a captured image, the apparatus does not perform averaging processing. This poses a problem: the obtained tomographic image is affected by irregular noise.

The OCT apparatus disclosed in Japanese Patent Laid-Open No. 2010-110392 averages a plurality of images captured in the same area to reduce the influence of irregular noise, and performs averaging processing of pixel values. The number of tomographic images to be obtained for the execution of this averaging processing is uniformly fixed. To perform averaging processing, it is necessary to capture a plurality of images in the same area. To obtain high-quality tomographic images, it is necessary to obtain a larger number of tomographic images. Although a captured image is segmented into a plurality of areas, averaging processing is not performed for each imaging area. In practice, therefore, unnecessary tomographic images may be obtained. This will lead to a longer imaging time and hence place a burden on an object to be examined.

In consideration of the above problems, the present invention provides a technique of shortening the time required for imaging and reducing the burden on a patient by decreasing the number of images to be obtained to obtain a high-quality tomographic image necessary for diagnosis.

SUMMARY OF THE INVENTION

According to one aspect of the present invention, there is provided an ophthalmic imaging apparatus which obtains a tomographic image of an eye to be examined based on light obtained by combining return light from the eye irradiated with measurement light with reference light corresponding to the measurement light, the apparatus comprising: a scanning unit configured to scan the measurement light on the eye; and a control unit configured to control the number of times of scanning by the scanning unit in accordance with a scanning position of the scanning unit on the eye.

According to one aspect of the present invention, there is provided a method of controlling an ophthalmic imaging apparatus which includes a scanning unit and a control unit, and obtains a tomographic image of an eye to be examined based on light obtained by combining return light from the eye irradiated with measurement light with reference light corresponding to the measurement light, the method comprising: causing the scanning unit to scan the measurement light on the eye; and causing the control unit to control the number of times of scanning by the scanning unit in accordance with a scanning position of the scanning unit on the eye.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
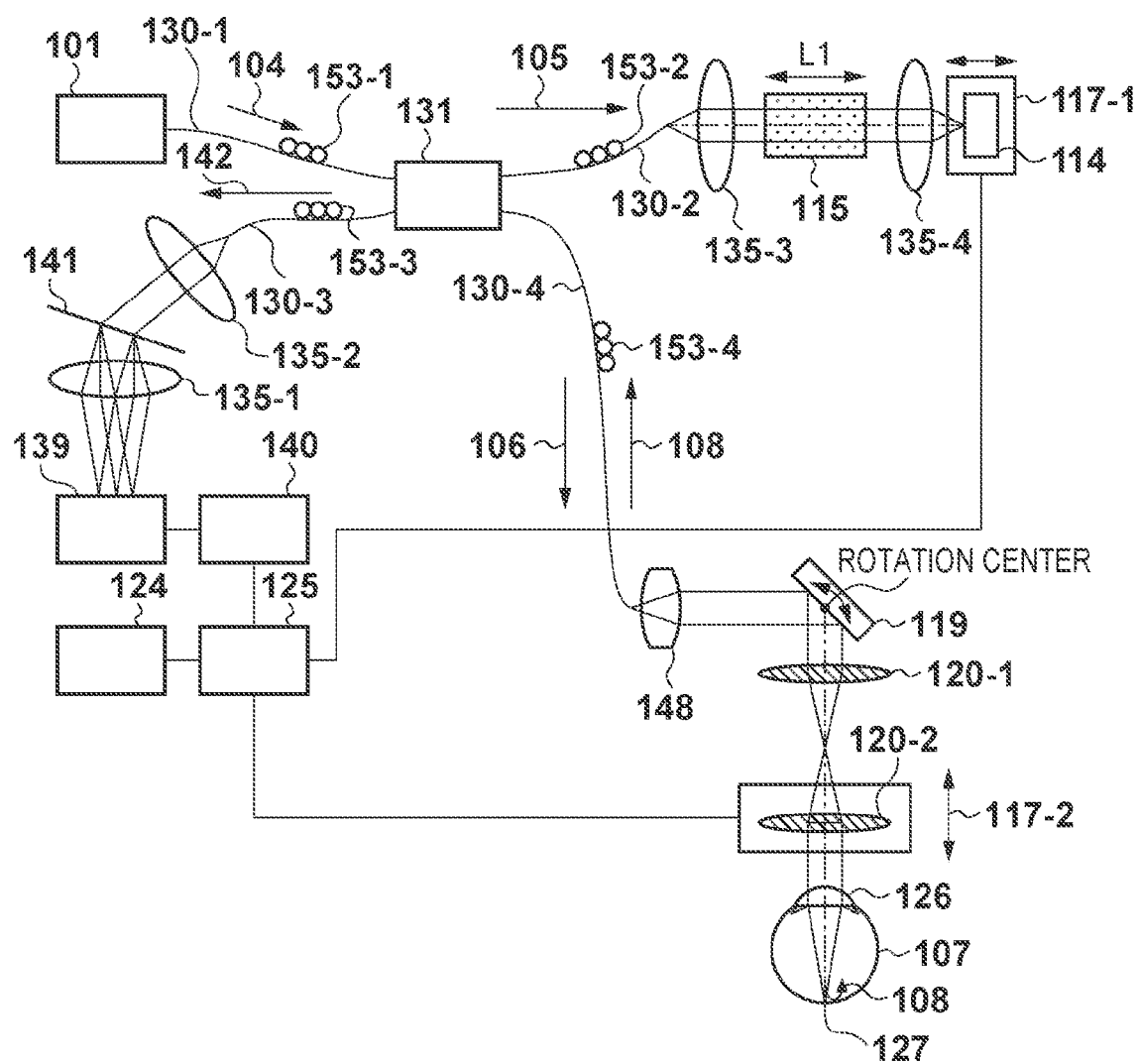
FIG. 1 is a view showing the arrangement of an OCT apparatus according to the first embodiment.

The first embodiment of the present invention will be described below with reference to FIGS. 1 to 5. FIG. 1 shows the arrangement of an OCT apparatus (ophthalmic imaging apparatus) according to the first embodiment. The OCT apparatus splits light from a light source into measurement light and reference light, and obtains a tomographic image of the eye to be examined based on the wavelength spectrum of interference light between the reference light and return light returning from the eye upon irradiating the eye with the measurement light. Reference numeral 101 denotes a light source; 104, exit light; 105, reference light; 106, measurement light; 142, composite light; 107, an eye to be examined; 108, return light, 130-1 to 130-4, single-mode fibers; 120-1, 120-2, and 135-1 to 135-4, lenses; 114, a mirror; 115, a dispersion-compensating glass; 117, an electrically-driven stage; 119, an XY scanner; 125, a personal computer; 124, a monitor; 126, a cornea; 127, a retina; 131, an optical coupler; 139, a line camera; 140, a frame grabber; 141, a transmission type diffraction grating; and 153-1 to 153-4, polarization controllers.

As a whole, the OCT apparatus according to this embodiment forms a Michelson interferometer system. The exit light 104 emitted from the light source 101 passes through the polarization controller 153-1. The optical coupler 131 splits the exit light 104 into the reference light 105 and the measurement light 106 at an intensity ratio of 50:50. The measurement light 106 returns as the return light 108 reflected or scattered by the retina 127 or the like of the eye 107 to be observed. The optical coupler 131 combines the return light 108 with the reference light 105 reflected by the mirror 114. After the reference light 105 is combined with the return light 108, the transmission type diffraction grating 141 spectrally separates the composite light for each wavelength. The resultant light strikes the line camera 139. The line camera 139 converts the light intensity into a voltage for each position (wavelength), and forms a tomographic image of the eye 107 by using the resultant voltage signal.

The light source 101 and the like will be described next. The light source 101 is an SLD (Super Luminescent Diode) which is a low-coherent light source. This light source has a wavelength of 830 nm and a bandwidth of 50 nm. In this case, the bandwidth influences the resolution of an obtained tomographic image in the optical axis direction, and hence is an important parameter. As the type of light source, SLD is selected in this case. However, an ASE (Amplified Spontaneous Emission) light source or the like can be used as long as it can emit low-coherent light. In consideration of measurement on the eyes, a near-infrared wavelength is suitable for this embodiment. Furthermore, since a wavelength influences the resolution of an obtained tomographic image in the horizontal direction, the shorter the wavelength, the better. Assume that in this case, the wavelength is 830 nm. Depending on the measurement region to be observed, other wavelengths may be selected.

The optical path of the reference light 105 will be described next. The reference light 105 split by the optical coupler 131 passes through the polarization controller 153-2 and emerges from the lens 135-3 as nearly parallel light having a diameter of 1 mm. The emerging reference light 105 passes through the dispersion-compensating glass 115. The lens 135-4 focuses the light onto the mirror 114. The mirror 114 changes the direction of the reference light 105, which then propagates to the optical coupler 131 through the same path. The reference light 105 whose direction is changed by the mirror 114 passes through the optical coupler 131 and is guided to the line camera 139.

In this case, the dispersion-compensating glass 115 compensates for the dispersion caused when the measurement light 106 reciprocates in the eye 107 with respect to the reference light 105. In this case, L1=23 mm, based on the premise of the diameter of the eyeball of the average Japanese person. An electrically-driven stage 117-1 can move in the directions indicted by the arrows in FIG. 1, and can adjust/control the position of the mirror 114. This can adjust/control the optical path length of the reference light 105. The personal computer 125 controls the electrically-driven stage 117-1 at high speed.

<Arrangement of Measurement Optical Path>

The optical path of the measurement light 106 will be described next. The measurement light 106 split by the optical coupler 131 passes through the polarization controller 153-4 and emerges from a lens 148 as nearly parallel light having a diameter of 1 mm. The light then strikes the mirror of the XY scanner 119. For the sake of simplicity, in this case, the XY scanner 119 is presented as one mirror. In practice, however, two mirrors, that is, an X scan mirror and a Y scan mirror, are disposed near each other to raster-scan on the retina 127 in a direction perpendicular to the optical axis. In addition, the lenses 120-1 and 120-2 and the like are adjusted such that the center of the measurement light 106 coincides with the rotation center of the mirror of the XY scanner 119. The lenses 120-1 and 120-2 constitute an optical system for scanning the measurement light 106 on the retina 127, which serves to scan the retina 127 with a point near the cornea 126 being a fulcrum point. The measurement light 106 is configured to be formed into an image on the retina 127.

An electrically-driven stage 117-2 can move in the directions indicted by the arrows in FIG. 1, and can adjust/control the position of the accompanying lens 120-2. Adjusting the position of the lens 120-2 will focus the measurement light 106 onto a desired layer of the retina 127 of the eye 107, thereby allowing observation. This technique can be applied to even a case in which the eye 107 has a refractive error. When the measurement light 106 strikes the eye 107, the light reflected and scattered by the retina 127 becomes the return light 108. The return light 108 passes through the optical coupler 131 along the same path and is guided to the line camera 139. The personal computer 125 controls the electrically-driven stage 117-2 at high speed.

<Arrangement of Spectroscopic Unit>

The arrangement of the measurement system of the OCT apparatus according to this embodiment will be described next. The optical coupler 131 combines the reference light 105 with the return light 108 which is light reflected and scattered by the retina 127. Composite light 142 emerges from a fiber end and passes through the polarization controller 153-3. The lens 135-2 collimates the light into nearly parallel light. The transmission type diffraction grating 141 is irradiated with this nearly parallel light and spectrally separates the light for each wavelength. The lens 135-1 focuses the separated light. The line camera 139 converts the light intensity into a voltage for each position (wavelength). Interference fringes in a spectral area on the wavelength axis are observed on the line camera 139. The spectroscopic unit will be described concretely below.

It is known that the OCT apparatus has the general characteristics that as the spectral width increases, the resolution of the OCT increases, whereas as the wavelength resolution in spectroscopy increases, the measurable width in the depth direction increases. These characteristics can be expressed by equations (1) and (2) given below:

$$R = \frac{1}{2\Delta K} \quad (1)$$

$$D = \frac{N}{2\Delta K} \quad (2)$$

where R is the resolution of the OCT, $\Delta K$ is the wavenumber width obtained by the line camera, D is the measurable width of the OCT in the depth direction, and N is the number of pixels of the line camera. Note that the spectral width is the range of wavelengths of light striking the N pixels of the line camera, and is a difference $\lambda_{max}-\lambda_{min}$ between a maximum wavelength $\lambda_{max}$ and a minimum wavelength $\lambda_{min}$. The wavenumber width $\Delta K$ is represented as $\Delta K=1/\lambda_{min}-1/\lambda_{max}$. The resolution of the OCT is generally defined as half of the coherence length. This indicates that as $\Delta K$ increases, R decreases (the resolution of the OCT decreases), whereas when N is constant, as $\Delta K$ decreases (the wavelength resolution in spectroscopy increases), D increases (the measurable width in the depth direction increases). In this case, the wavelength resolution is the wavelength width obtained per pixel by dividing the spectral width by the number of pixels of the line camera. In general, the actual wavelength resolution is larger than the wavelength resolution defined in this case due to the optical aberrations of the lens.

The frame grabber 140 converts the voltage signals, obtained by converting the light intensities into voltages using the line camera 139, into digital values. The personal computer 125 forms a tomographic image by performing data processing of the digital values. In this case, the line camera 139 has 1024 pixels, and can obtain the intensity of the composite light 142 for each wavelength.

<Method of Obtaining Tomographic Image>

Figure 4A:
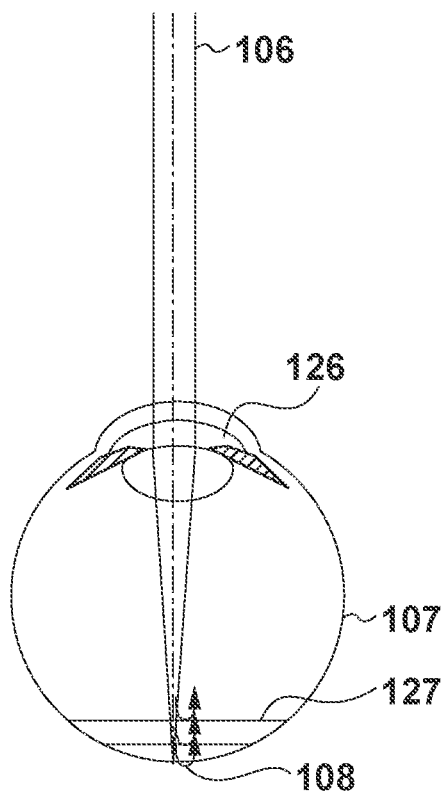
FIGS. 4A to 4C are views for explaining a method of obtaining tomographic images using the OCT apparatus according to the first embodiment.

A method of obtaining a tomographic image (a plane parallel to the optical axis) of the retina 127 by using the OCT apparatus will be described next with reference to FIGS. 4A to 4C. FIG. 4A shows how the eye 107 is observed with the OCT apparatus. The same reference numerals as in FIG. 1 denote the same or corresponding constituent elements in FIG. 4, and a repetitive description will be omitted. As shown in FIG. 4A, the measurement light 106 strikes the retina 127 through the cornea 126. This light is reflected and scattered at various positions thereafter to become the return light 108. The return light 108 reaches the line camera 139 with time delays at the respective positions.

In this case, since the bandwidth of the light source 101 is large and the spatial coherence length is short, when the optical length of reference light is almost equal to that of measurement light, the line camera 139 detects interference fringes. As described above, the interference fringes obtained by the line camera 139 are those in a spectral area on the wavelength axis. These interference fringes as information on the wavelength axis are converted into interference fringes on the optical frequency axis for each composite light 142 in consideration of the characteristics of the line camera 139 and transmission type diffraction grating 141. In addition, performing inverse Fourier transform for the converted interference fringes on the optical frequency axis will obtain information in the depth direction.

Figure 4B:
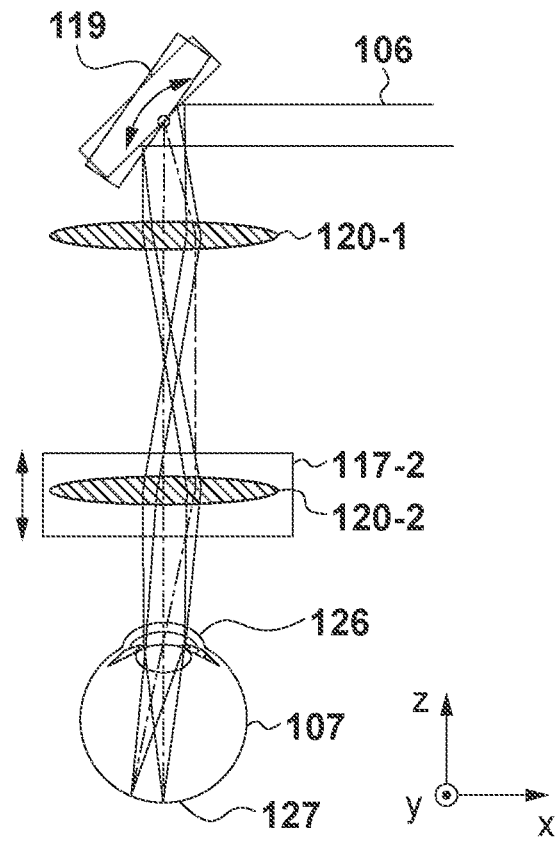
Figure 4C:
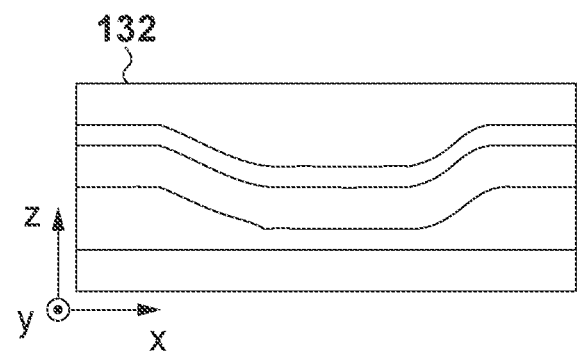

As shown in FIG. 4B, it is possible to obtain interference fringes for each X-axis position by detecting the interference fringes while driving the X-axis of the XY scanner 119. That is, it is possible to obtain information in the depth direction for each X-axis position. As a result, a two-dimensional distribution of the intensities of the return light 108 on an X-Z plane is obtained. This two-dimensional distribution is a tomographic image 132 as shown in FIG. 4C. The tomographic image 132 is basically an array of the intensities of the return light 108, as described above, and is displayed by mapping the intensities on a grayscale. In this case, only the boundaries of the obtained tomographic image are emphasized and displayed.

Figure 2A:
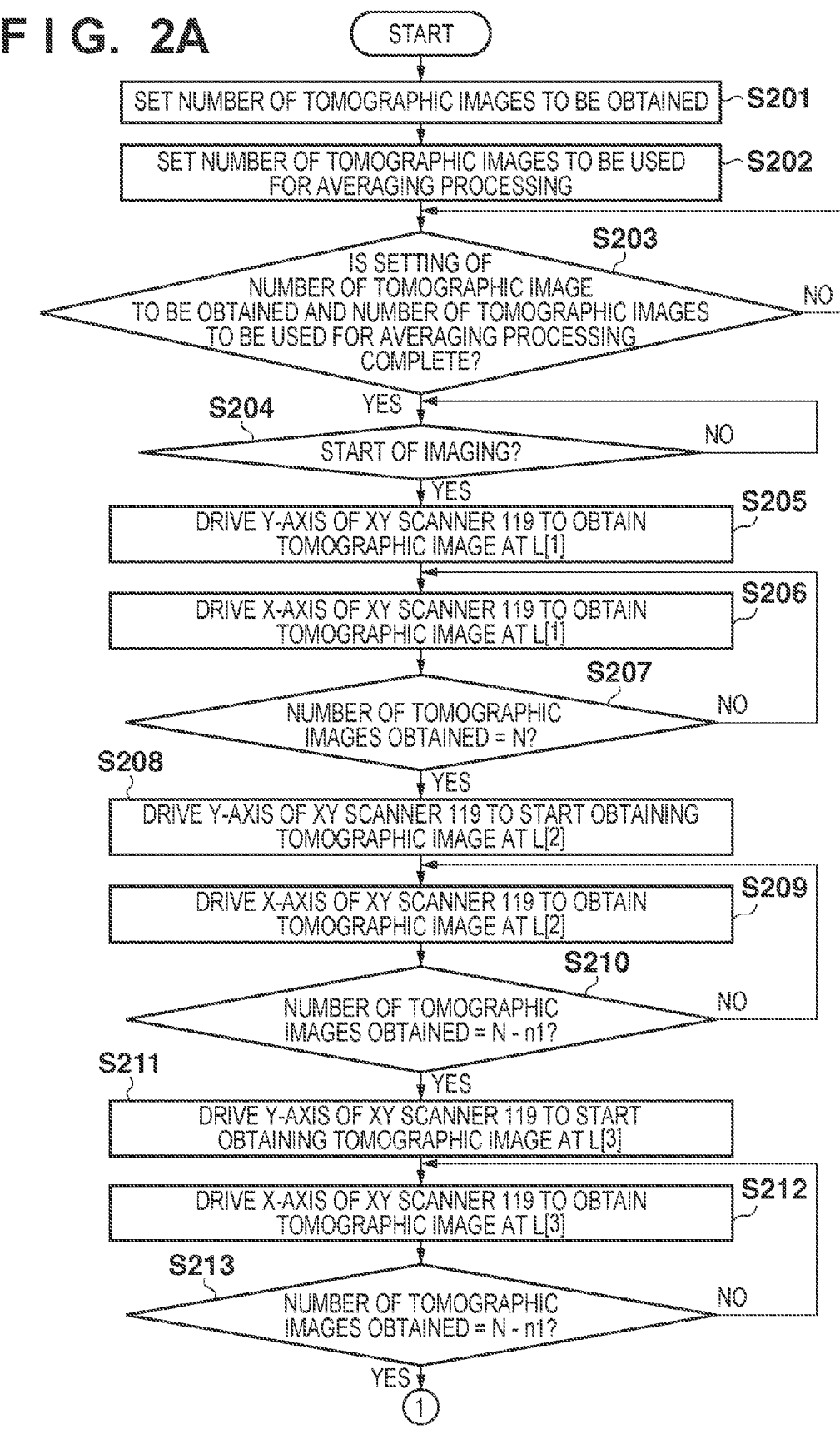
FIGS. 2A to 2B are flowcharts showing a processing procedure for obtaining tomographic images using the OCT apparatus according to the first embodiment.
Figure 2B:
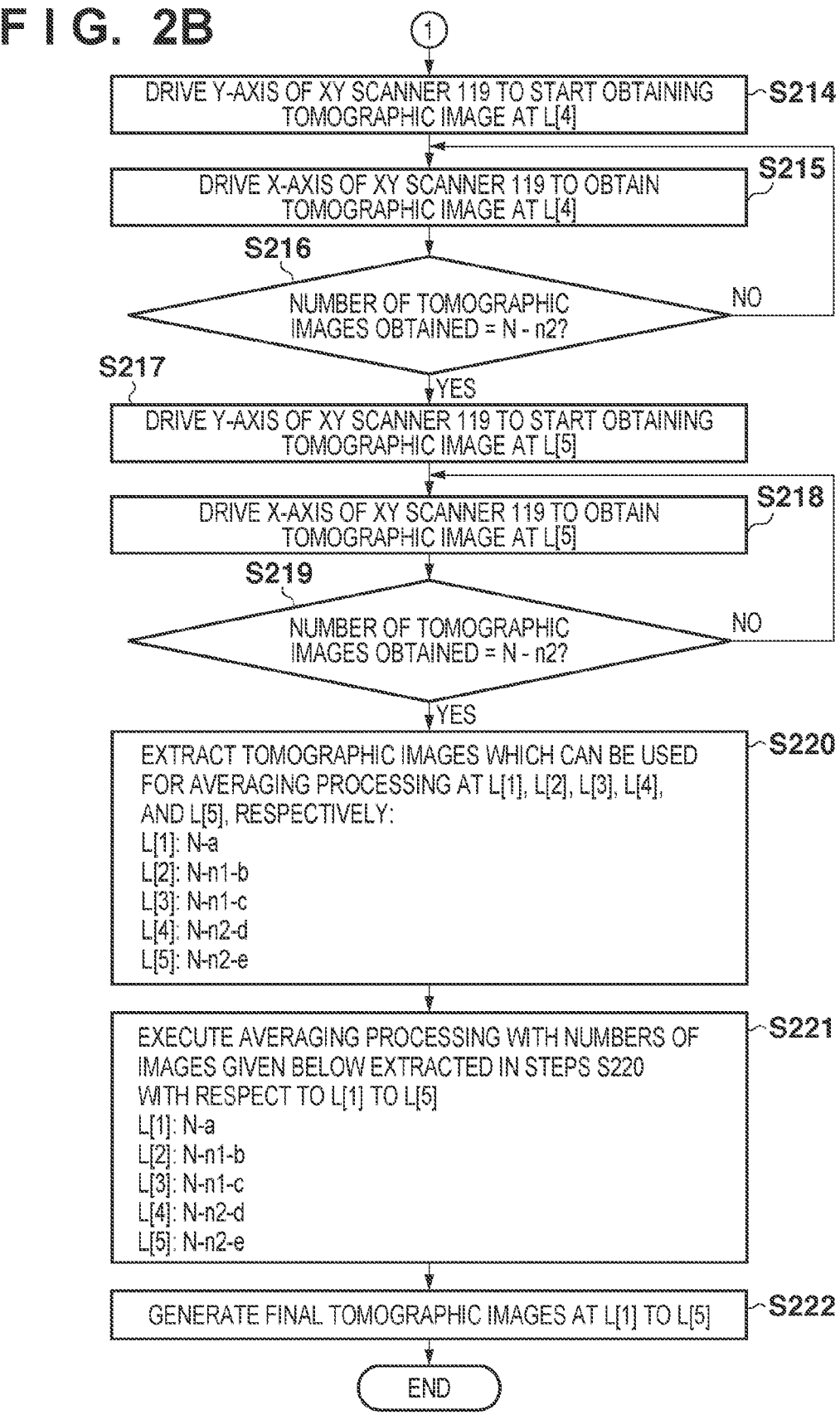

A processing procedure in a method of obtaining tomographic images by using the OCT apparatus according to this embodiment will be described next with reference to FIGS. 2A and 2B. FIGS. 2A and 2B are a flowchart showing processing operation performed by the CPU of the personal computer 125. The following is a case in which the apparatus performs B-scan at each of five scanning regions L1 to L5 which are a plurality of scanning areas on the eye to be examined, as a position at which the eye is irradiated with measurement light, as indicated by "3001" in FIG. 3.

Figure 5:
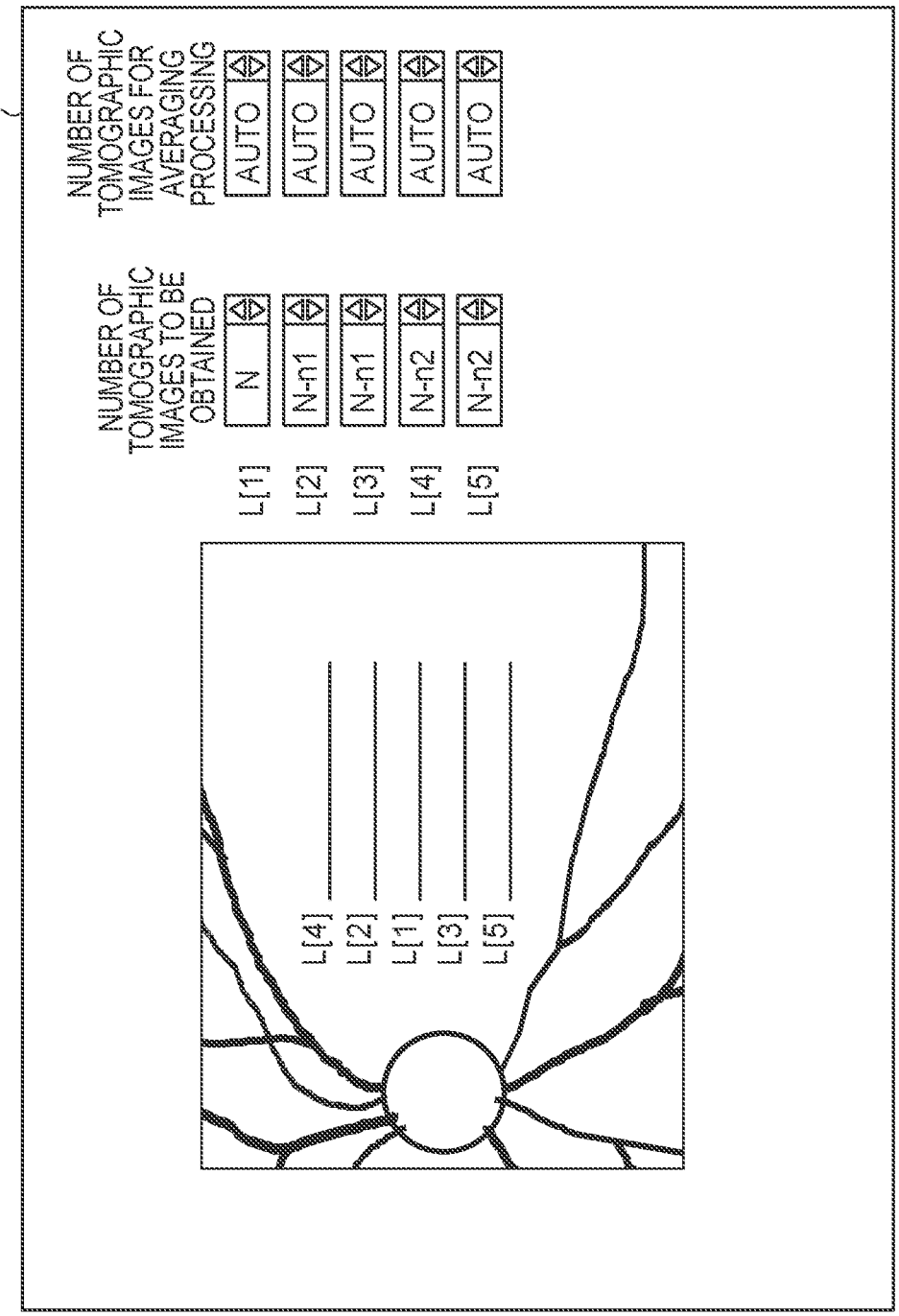
FIG. 5 is a view showing the display screen of a monitor 124 according to the first embodiment.

In step S201, the operator sets the number of tomographic images to be obtained at each scanning region on an input window 501 shown in FIG. 5. To set the number of tomographic images to be obtained is equivalent to setting the number of times of scanning. At first, the number of tomographic images to be obtained is set to a predetermined number in advance, and the operator can change the number of tomographic images to be obtained for each scanning region. In this embodiment, the numbers of tomographic images to be obtained are set as follows: L[1]: N, L[2] and L[3]: N-n1, and L[4] and L[5]: N-n2. That is, of the plurality of scanning areas on the eye 107, a large number of tomographic images to be obtained are set at L[1] near the central position of the eye 107 (for example, a scanning position in the central portion), and a small number of tomographic images to be obtained are set at L[4] and L[5] near peripheral positions of the eye (for example, peripheral positions far from the scan center).

In step S202, the operator sets the number of tomographic images to be used for tomographic image averaging processing on the input window 501. At first, the number of tomographic images to be used for averaging processing is set to a predetermined number in advance, and the operator can change the number of times of scanning for each scanning region with an input acceptance unit. In this embodiment, L[1], L[2], L[3], L[4], and L[5] are all set to "AUTO". That is, the CPU automatically determines the quality of each of the number of tomographic images to be obtained which is set in step S201, and performs the processing of adding and averaging only the necessary tomographic images.

In step S203, the CPU determines whether setting of the number of tomographic images to be obtained for each scanning region and setting of the number of tomographic images to be used for averaging processing are complete. If the CPU determines that the setting of these numbers is complete (YES in step S203), the process advances to step S204. If the CPU determines that the setting of these numbers is not complete (NO in step S203), the process waits for the completion of the setting.

In step S204, the CPU detects the presence/absence of the input of an imaging start instruction by the operator to determine whether the operator has input an imaging start instruction. If the CPU determines that the operator has input an imaging start instruction (YES in step S204), the process advances to step S205. If the CPU determines that the operator has not input an imaging start instruction (NO in step S204), the process waits until the operator inputs an imaging start instruction.

In step S205, the CPU drives the XY scanner 119 in the Y-axis direction to a position to obtain a tomographic image at the scanning region L[1].

In step S206, the CPU drives the XY scanner 119 in the X-axis direction to obtain a tomographic image at the scanning region L[1] in the X-axis direction (horizontal direction).

In step S207, the CPU determines whether the number of tomographic images to be obtained at the scanning region L[1] has reached a preset number N. As indicated by "3002" in FIG. 3, if the CPU determines that the number of tomographic image to be obtained has reached N (YES in step S207), the process advances to step S208. If the CPU determines that the number of tomographic images to be obtained has not reached N (NO in step S207), the process returns to step S206.

In step S208, the CPU drives the XY scanner 119 in the Y-axis direction to a position to obtain a tomographic image at the scanning region L[2].

In step S209, the CPU drives the XY scanner 119 in the X-axis direction to obtain a tomographic image at the scanning region L[2] in the X-axis direction (horizontal direction). In step S210, the CPU determines whether the number of tomographic images to be obtained at the scanning region L[2] has reached a preset number N-n1. As indicated by "3002" in FIG. 3, if the CPU determines that the number of tomographic image to be obtained has reached N-n1 (YES in step S210), the process advances to step S211. If the CPU determines that the number of tomographic images to be obtained has not reached N-n1 (NO in step S210), the process returns to step S209.

In step S211, the CPU drives the XY scanner 119 in the Y-axis direction to a position to obtain a tomographic image at the scanning region L[3]. In addition, in step S212, the CPU drives the XY scanner 119 in the X-axis direction to obtain a tomographic image at the scanning region L[3] in the X-axis direction (horizontal direction).

In step S213, the CPU determines whether the number of tomographic images to be obtained at the scanning region L[3] has reached a preset number N-n1. As indicated by "3002" in FIG. 3, if the CPU determines that the number of tomographic images to be obtained has reached N-n1 (YES in step S213), the process advances to step S214. If the CPU determines that the number of tomographic images to be obtained has not reached N-n1 (NO in step S213), the process returns to step S212.

In step S214, the CPU drives the XY scanner 119 in the Y-axis direction to a position to obtain a tomographic image at the scanning region L[4]. In addition, in step S215, the CPU drives the XY scanner 119 in the X-axis direction to obtain a tomographic image at the scanning region L[4] in the X-axis direction (horizontal direction).

In step S216, the CPU determines whether the number of tomographic images to be obtained at the scanning region L[4] has reached a preset number N-n2. As indicated by "3002" in FIG. 3, if the CPU determines that the number of tomographic images to be obtained has reached N-n2 (YES in step S216), the process advances to step S217. If the CPU determines that the number of tomographic images to be obtained has not reached N-n2 (NO in step S216), the process returns to step S215.

In step S217, the CPU drives the XY scanner 119 in the Y-axis direction to a position to obtain a tomographic image at the scanning region L[5]. In addition, in step S218, the CPU drives the XY scanner 119 in the X-axis direction to obtain a tomographic image at the scanning region L[5] in the X-axis direction (horizontal direction).

In step S219, the CPU determines whether the number of tomographic images to be obtained at the scanning region L[5] has reached a preset number N-n2. As indicated by "3002" in FIG. 3, if the CPU determines that the number of tomographic image to be obtained has reached N-n2 (YES in step S219), the process advances to step S220. If the CPU determines that the number of tomographic images to be obtained has not reached N-n2 (NO in step S219), the process returns to step S215.

In step S220, the CPU extracts tomographic images which can be used for averaging processing from the tomographic images at the scanning regions L[1], L[2], L[3], L[4], and L[5] which correspond to the numbers of times of scanning. In this extraction processing, the CPU may extract all the tomographic images obtained at the scanning regions L[1], L[2], L[3], L[4], and L[5].

In addition, the CPU may calculate S/N (Signal/Noise) ratios indicating the ratios between signal amounts (signal levels) and noise (noise levels) from the respective tomographic images at the scanning regions L[1], L[2], L[3], L[4], and L[5]. The CPU may extract some of the tomographic images of the respective scanning regions based on the calculated S/N ratios (S/N ratios).

If an S/N ratio is higher than a predetermined value, that is, noise is small, even a small number of tomographic images used for averaging processing allow obtainment of a high-quality tomographic image. It is therefore possible to decrease the number of tomographic images to be extracted. In contrast, if the S/N ratio is equal to or less than the predetermined value, that is, noise is large, it is not possible to obtain a high-quality tomographic image from a small number of tomographic images used for averaging processing. In this case, it is necessary to increase the number of tomographic images to be extracted.

For example, the CPU may quantify and classify the S/N values into 10 levels from the first to 10th levels, and decide the numbers of tomographic images to be extracted in accordance with the levels.

Figure 3:
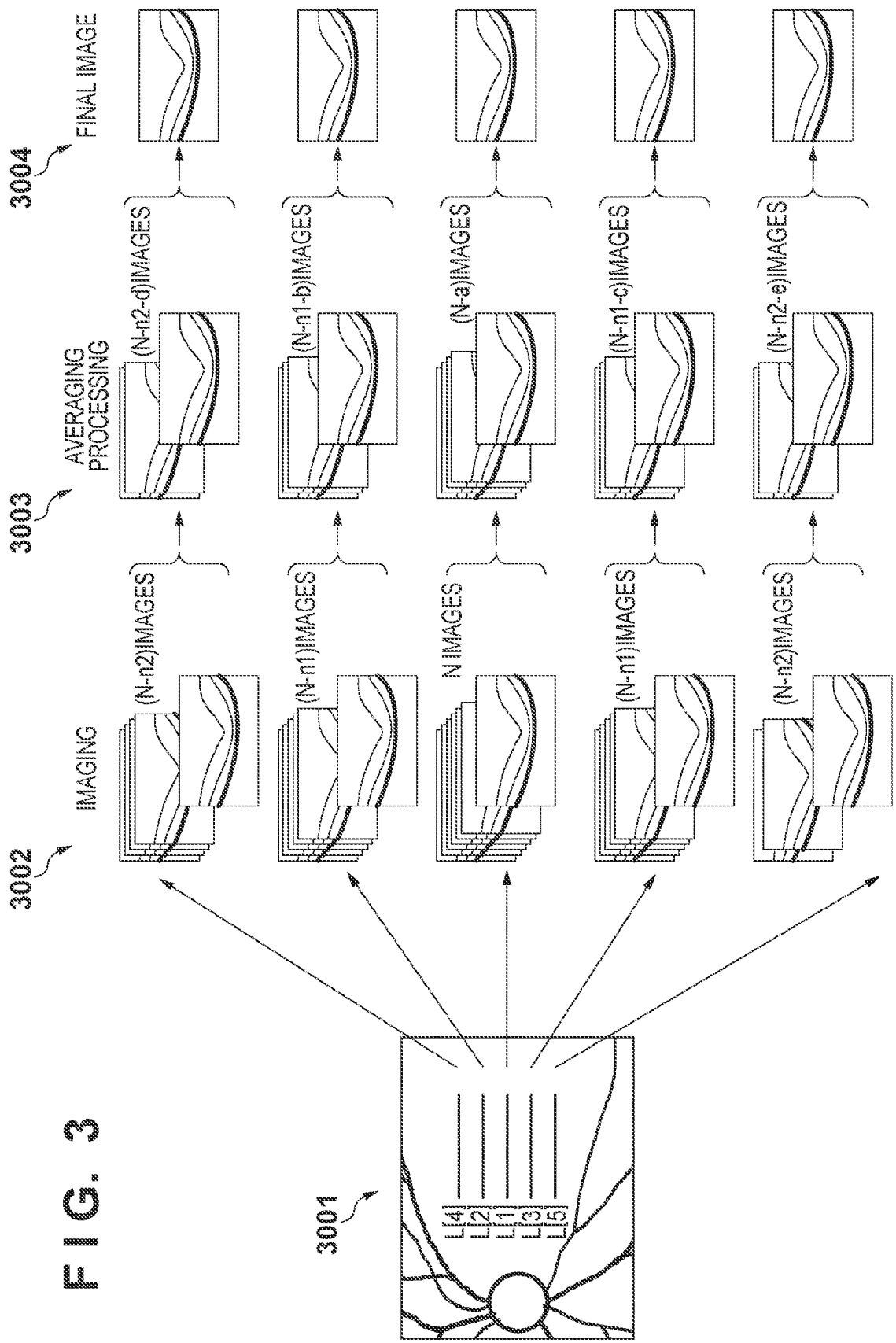
FIG. 3 is a flowchart showing the operation of a personal computer 125 according to the first embodiment.

Assume that, as indicated by "3003" in FIG. 3, the extraction results in this embodiment are: L[1]: N-a images, L[2]: N-n1-b images, L[3]: N-n1-c images, L[4]: N-n2-d images, and L[5]: N-n2-e images. Note that when all the tomographic images are to be extracted, a, b, c, d, and e are 0. In contrast, when some of the tomographic images are to be extracted, these values are decided in accordance with the above S/N values.

In step S221, the CPU performs averaging processing by using the tomographic images extracted in step S220 with respect to each of the scanning regions L[1], L[2], L[3], L[4], and L[5]. In step S222, the CPU outputs the final tomographic images like those indicated by "3004" in FIG. 3. With the above operation, the CPU terminates the processing.

The manner in which this embodiment can shorten the time taken to obtain tomographic images will be described with reference to a concrete example. When the CPU obtains the same number N of tomographic images at each of all the five scanning regions L[1], L[2], L[3], L[4], and L[5] assuming that the data obtaining rate of the line camera 139 is set to R=70000 data/sec, number N of tomographic images to be obtained=10, and the number of times of scanning at each scanning region L is set to B=1024, a time T1 required for tomographic image obtaining processing is calculated by $$T1 = B \times N \times 5/R = 1024 \times 10 \times 5/70000 = 0.73 \text{ [sec]} \quad (3)$$

When changing the number of tomographic images to be obtained for each scanning region as in this embodiment with n1=4 and n2=6, a time T2 required to obtain tomographic images is calculated by $$\begin{aligned} T2 &= B \times \{N + (N-n1) \times 2 + (N-n2) \times 2\}/R \\ &= 1024 \times \{10 + (10-4) \times 2 + (10-6) \times 2\}/70000 \\ &= 0.44 \text{ [sec]} \end{aligned} \quad (4)$$

That is, according to this embodiment, the time required to obtain tomographic images is calculated by T2−T1. That is, the embodiment can shorten the time required to obtain tomographic images by about 0.3 sec. Assuming that the imaging time is fixed, and the overall imaging time is almost equal to the time taken to obtain tomographic images, the number of tomographic images to be obtained may be decided for each scanning region.

If imaging time=tomographic image obtaining time=T3 and T3≤1 sec, a total number M of the numbers of times tomographic images are obtained at the respective scanning regions is calculated by using T3, the data obtaining rate R, and the scan count B according to $$\begin{aligned} M &\leq T3 \times R/B \\ &= 1 \times 70000/1024 \\ &\leq 68 \end{aligned} \quad (5)$$

A maximum 68 times of measurement may be assigned to the scanning regions L[1], L[2], L[3], L[4], and L[5] according to the calculation result of expression (5) as follows: L[1]: 20 images, L[2]: 13 images, L[3]: 13 images, L[4]: 11 images, and L[5]: 11 images.

As described above, the present invention can shorten the time required for imaging and reduce the burden on a patient by decreasing the number of images to be obtained to obtain a high-quality tomographic image necessary for diagnosis.

Second Embodiment

Figure 6:
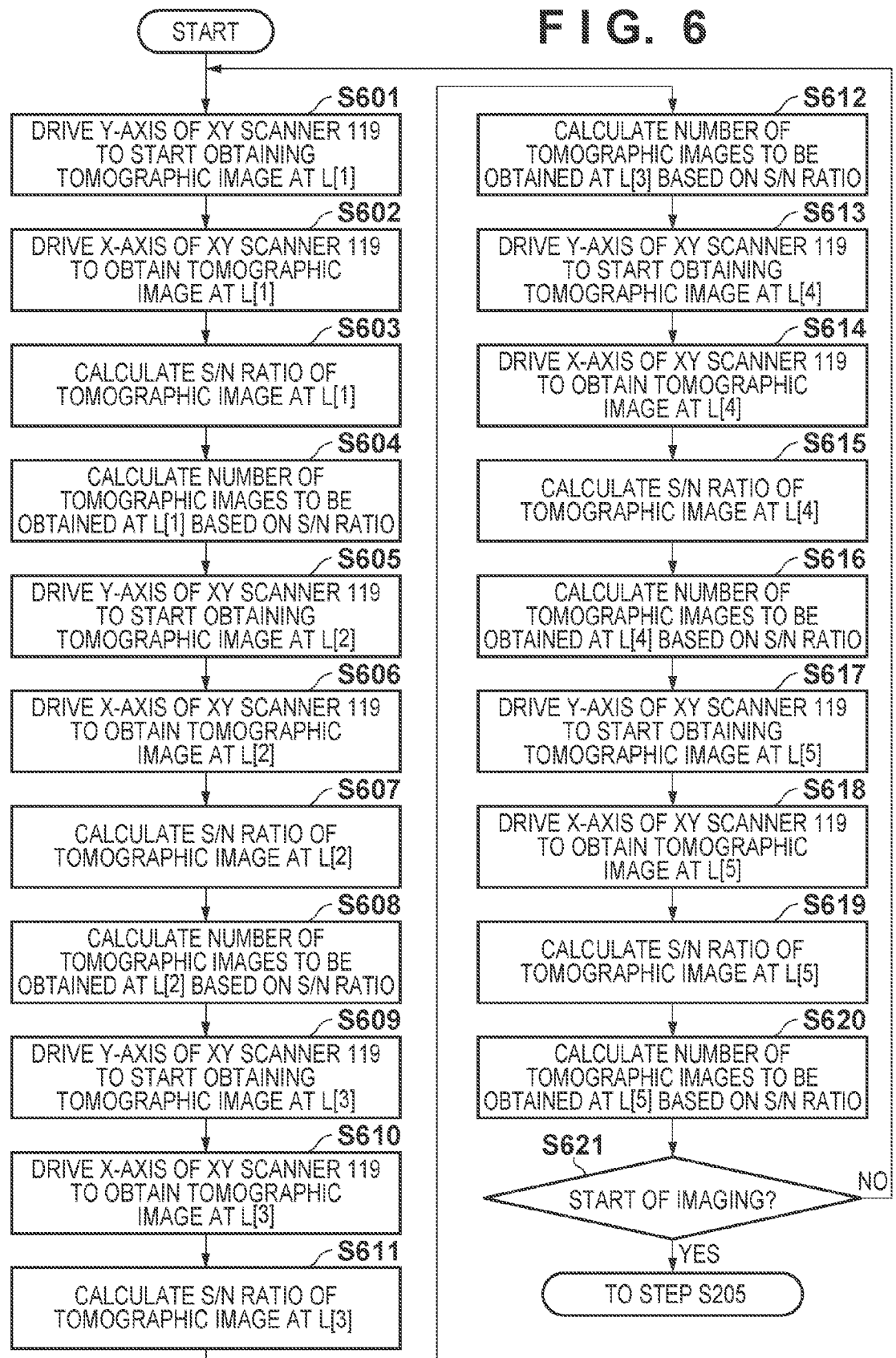
FIG. 6 is a flowchart showing the operation of a personal computer 125 according to the second embodiment.

The second embodiment of the present invention will be described with reference to FIG. 6. The arrangement of an OCT apparatus according to the second embodiment is the same as that of the OCT apparatus shown in FIG. 1 described in the first embodiment, and hence a description of the arrangement will be omitted. FIG. 6 is a flowchart showing the processing operation performed by the CPU of a personal computer 125 according to the second embodiment. The processing in each of steps S201 to S204 described with reference to the flowcharts of FIGS. 2A and 2B is changed to that in each of steps S601 to S621.

In step S601, the CPU drives an XY scanner 119 in the Y-axis direction to a position to obtain a tomographic image at a scanning region L[1].

In step S602, the CPU drives the XY scanner 119 in the X-axis direction to obtain a tomographic image at the scanning region L[1] in the X-axis direction (horizontal direction).

In step S603, the CPU calculates an S/N (Signal/Noise) ratio from the tomographic image at the scanning region L[1] obtained in step S602.

In step S604, the CPU determines the number of tomographic images to be obtained at the scanning region L[1] based on the S/N ratio calculated in step S603. If the S/N ratio is higher than a predetermined value, that is, noise is small, even a small number of tomographic images used for averaging processing allows obtainment of a high-quality tomographic image. It is therefore possible to decrease the number of tomographic images to be obtained. In contrast, if an S/N ratio is equal to or less than the predetermined value, that is, noise is large, it is not possible to obtain a high-quality tomographic image from a small number of tomographic images used for averaging processing. In this case, it is necessary to increase the number of tomographic images to be obtained.

For example, the CPU may quantify and classify the S/N values into 10 levels from the first to 10th levels, and decide the numbers of tomographic images to be obtained in accordance with the levels. If the S/N ratio is higher than the predetermined value, it is possible to execute no averaging processing by setting the number of tomographic images to be obtained to 1. As in the case of the scanning region L[1], the CPU drives the XY scanner 119 in the Y-axis direction to obtain tomographic images at scanning regions L[2], L[3], L[4], and L[5] in steps S605, S609, S613, and S617.

In steps S616, S610, S614, and S618, the CPU drives the XY scanner 119 in the X-axis direction to obtain tomographic images at the scanning regions L[2], L[3], L[4], and L[5] in the X-axis direction (horizontal direction).

In steps S607, S611, S615, and S619, the CPU calculates S/N ratios from the tomographic images at the scanning regions L[2], L[3], L[4], and L[5] obtained in steps S616, S610, S614, and S618.

In steps S608, S612, S616, and S620, the CPU decides the numbers of tomographic images to be obtained at the scanning regions L[2], L[3], L[4], and L[5] based on the calculated S/N ratios.

When the CPU completes the processing in step S620, the process advances to step S621. In step S621, the CPU detects the presence/absence of the input of an imaging start instruction by the operator to determine whether the operator has input an imaging start instruction. If the CPU determines that the operator has input an imaging start instruction (YES in step S621), the CPU terminates the processing. The process then advances to step S205. If the CPU determines that the operator has not input an imaging start instruction (NO in step S621), the process returns to step S601. Note that this arrangement is configured to return to step S601. However, the arrangement may be configured to wait until an imaging start instruction is input.

In this embodiment, the CPU detects S/N ratios and decides the numbers of tomographic images to be obtained in accordance with the S/N values. In contrast, a normal eye database may be mounted in the apparatus in advance to detect a lesion portion of the eye to be examined instead of detecting S/N ratios and decide the numbers of tomographic images to be obtained at the scanning regions L[1], L[2], L[3], L[4], and L[5] in accordance with the state of the detected lesion portion. In this case, for example, the CPU may decide a large number of tomographic images to be obtained at a scanning region in which a lesion portion is detected, and may decide a small number of tomographic images to be obtained at a scanning region in which no lesion portion is detected.

As described above, the present invention can shorten the time required for imaging and reduce the burden on a patient by decreasing the number of images to be obtained to obtain a high-quality tomographic image necessary for diagnosis.

Third Embodiment

Figure 7:
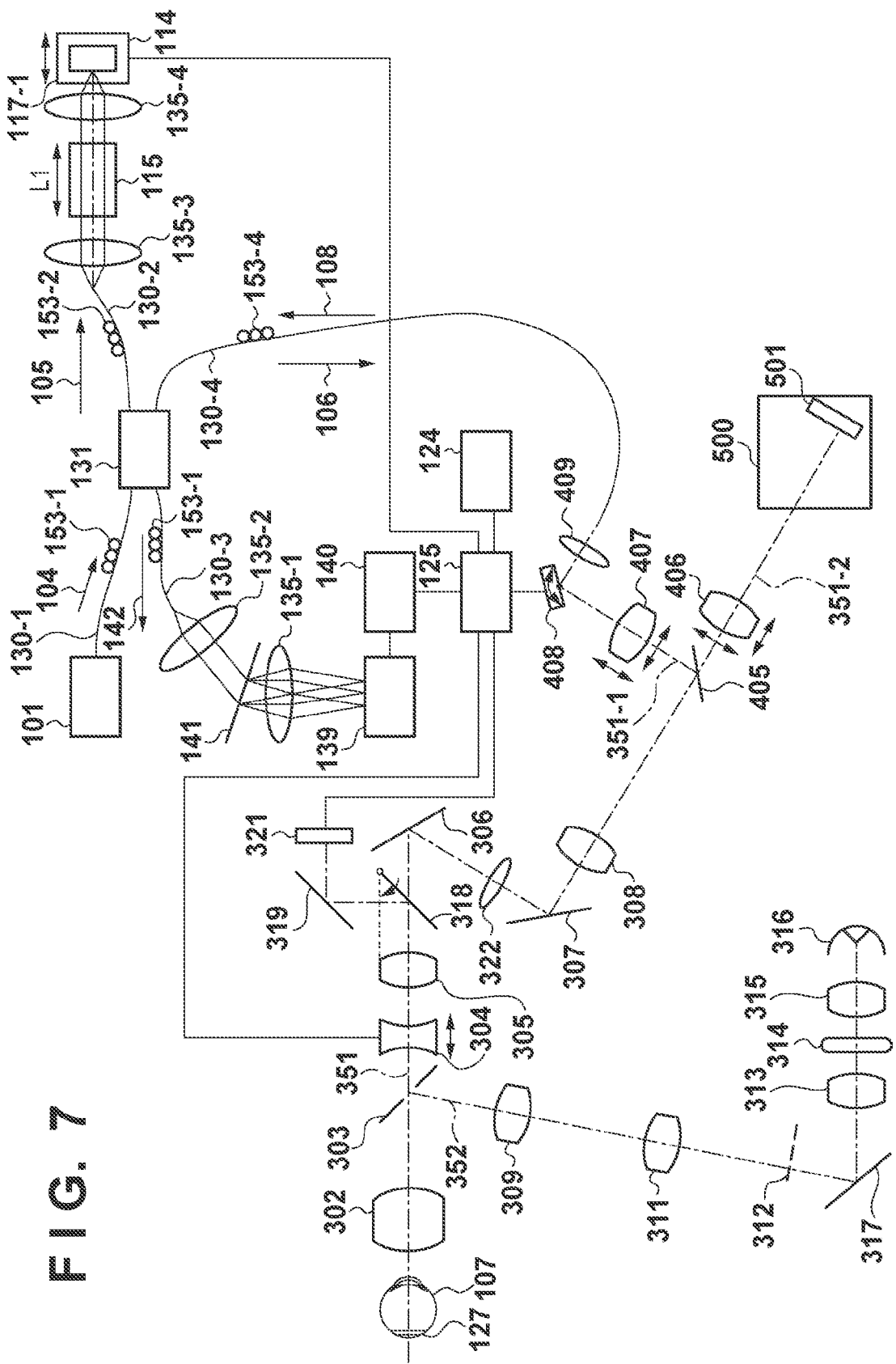
FIG. 7 is a view showing the arrangement of an OCT apparatus according to the third embodiment.
Figure 8:
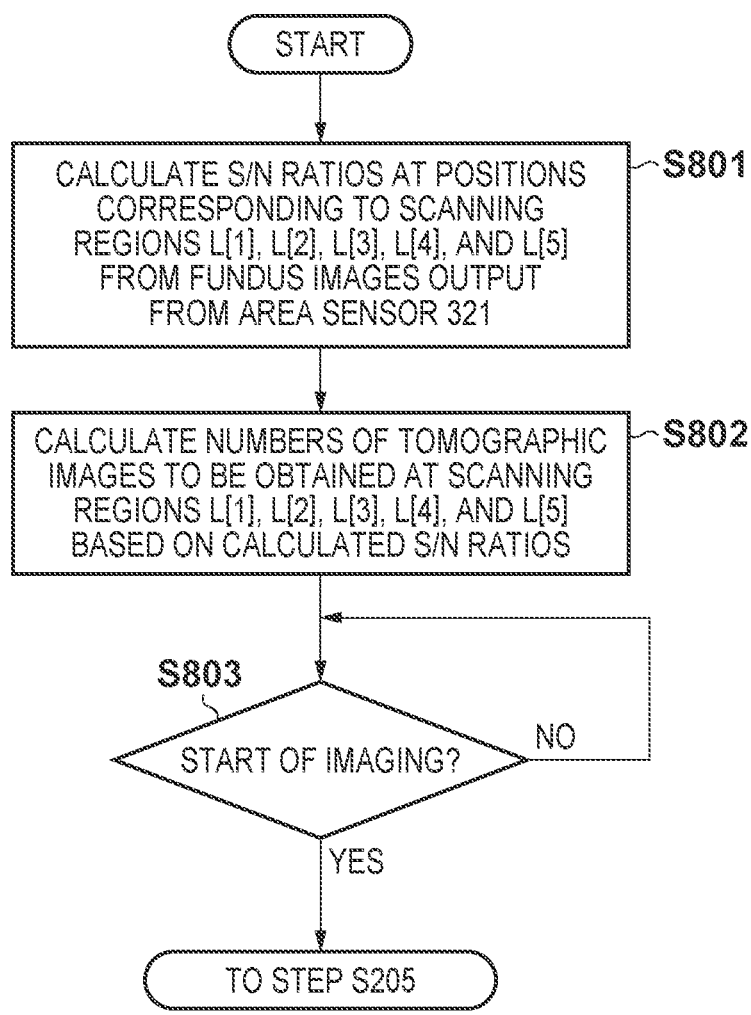
FIG. 8 is a flowchart showing the operation of a personal computer 125 according to the third embodiment.

The third embodiment of the present invention will be described with reference to FIGS. 7 and 8. FIG. 7 shows the arrangement of an OCT apparatus according to the third embodiment. Note that the same reference numerals as in FIG. 1 denote the same constituent elements in FIG. 7.

An objective lens 302 is disposed to face an eye 107 to be examined. A perforated mirror 303 provided on the optical axis splits light into an optical path 351 and an optical path 352.

The optical path 352 forms an illumination optical system which illuminates the fundus of the eye 107. The illumination optical system includes a halogen lamp 316, a strobe tube 314, a lens 309, a lens 311, an optical filter 310, a ring slit 312, a condenser lens 313, a condenser lens 315, and a mirror 317. The halogen lamp 316 is used to position the eye 107. The strobe tube 314 is used to image the fundus of the eye 107. The ring slit 312 forms illumination light from the halogen lamp 316 and the strobe tube 314 into a ring-like light beam. The perforated mirror 303 reflects the light beam to illuminate the fundus of the eye 107.

On the other hand, the optical path 351 forms an imaging optical system which captures a tomographic image of the fundus of the eye 107 and a fundus image. Referring to FIG. 7, a focus lens 304 and an imaging lens 305 are disposed on the right side of the perforated mirror 303. In this case, the focus lens 304 is supported to be movable in the optical axis direction. A personal computer 125 controls the position of the focus lens 304. The optical path 351 is guided to an area sensor 321 through a quick return mirror 318. In this case, the quick return mirror 318 is designed to reflect and transmit parts of infrared light and reflect visible light. Since the quick return mirror 318 is designed to reflect and transmit parts of infrared light, it is possible to simultaneously use a fixation lamp, the area sensor 321, and an OCT imaging unit. A mirror 319 is designed to form reflected light into an image on the area sensor 321. Light passing through the optical path 351 is guided to a dichroic mirror 405 through a mirror 306, a field lens 322, a mirror 307, and a relay lens 308.

The area sensor 321 is connected to the personal computer 125 to allow the personal computer 125 to capture a fundus image.

The dichroic mirror 405 splits the optical path 351 into an optical path 351-1 for tomographic image capturing operation and an optical path 351-2 for fundus image capturing operation. In this case, a relay lens 406 and a relay lens 407 are movably held. Finely adjusting the positions of the relay lenses 406 and 407 can adjust the optical axes of the optical path 351-1 and optical path 351-2. In this case, for the sake of simplicity, the XY scanner 408 is presented as one mirror. In practice, however, two mirrors, that is, an X scan mirror and a Y scan mirror, are disposed near each other to raster-scan on a retina 127 of the eye 107 in a direction perpendicular to the optical axis. In addition, the personal computer 125 controls the XY scanner 408. The optical axis of the optical path 351-1 is adjusted to coincide with the rotation center of the two mirrors of the XY scanner 408.

A camera unit 500 is a digital single-lens reflex camera for capturing a fundus image, and forms a fundus image on the surface of an area sensor 501. A collimate lens 409 is connected to a single-mode fiber 130-4. Since other arrangements are the same as those in FIG. 1, a description of them will be omitted.

Illumination light from the halogen lamp 316 passes through the condenser lens 315 and the condenser lens 313 and is reflected by the mirror 317. The ring slit 312 then forms the light into a ring-like light beam. This light beam passes through the lens 309 and the lens 311 and is reflected by the perforated mirror 303. The light then passes through the objective lens 302 and illuminates the fundus of the eye 107.

Reflected light from the retina 127 of the eye 107 passes through the objective lens 302 and passes through the hole portion of the perforated mirror 303. The light is reflected by the quick return mirror 318 and the mirror 319 and passes through the focus lens 304 and the imaging lens 305 to be formed into an image as an image of the eye on the area sensor 321. The personal computer 125 captures the fundus image formed on the area sensor 321.

The operation of the personal computer 125 according to the third embodiment will be described next with reference to the flowchart of FIG. 8. The processing in each of steps S201 to S204 described with reference to the flowcharts of FIGS. 2A and 2B is changed to that in each of steps S801 to S803.

In step S801, the CPU calculates S/N ratios at positions corresponding to scanning regions L[1], L[2], L[3], L[4], and L[5] from the fundus images captured by the personal computer 125 and output from the area sensor 321.

In step S802, the CPU decides the numbers of tomographic images to be obtained at the scanning regions L[1], L[2], L[3], L[4], and L[5] based on the calculated S/N ratios. This embodiment uses the same determination criterion used for decisions as that in the second embodiment.

In step S803, the CPU detects the presence/absence of the input of an imaging start instruction by the operator to determine whether the operator has input an imaging start instruction. If the CPU determines that the operator has input an imaging start instruction (YES in step S803), the process advances to step S205. If the CPU determines that the operator has not input an imaging start instruction (NO in step S803), the process returns to step S801. With the above operation, the CPU terminates the processing shown in FIG. 8.

In this embodiment, the CPU detects S/N ratios and decides the numbers of tomographic images to be obtained in accordance with the S/N values. In contrast, a normal eye database may be mounted in the apparatus in advance to detect a lesion portion of the eye to be examined instead of detecting S/N ratios and decide the numbers of tomographic images to be obtained at the scanning regions L[1], L[2], L[3], L[4], and L[5] in accordance with the state of the detected lesion portion. In this case, for example, the CPU may decide a large number of tomographic images to be obtained at a scanning region in which a lesion portion is detected, and may decide a small number of tomographic images to be obtained at a scanning region in which no lesion portion is detected.

As has been described above, the present invention can shorten the time required for imaging and reduce the burden on a patient by decreasing the number of images to be obtained to obtain a high-quality tomographic image necessary for diagnosis.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-079801 filed on Mar. 31, 2011, which is hereby incorporated by reference herein in its entirety.

What is claimed is:

1. An ophthalmic imaging apparatus which obtains a tomographic image of an eye to be examined based on light obtained by combining (a) return light from the eye irradiated with measurement light with (b) reference light corresponding to the measurement light, the apparatus comprising:
a scanning unit configured to scan the measurement light on the eye;
a control unit configured to control the number of times of scanning by said scanning unit in accordance with a scanning position of said scanning unit on the eye; and
an averaging unit configured to add and average tomographic images of the eye which are obtained at the scanning position,
wherein the scanning position includes positions of a plurality of scanning areas scanned by said scanning unit in the eye,
wherein said control unit comprises (a) a decision unit configured to decide the number of times of scanning by said scanning unit with respect to each of the plurality of scanning areas based on the positions of the plurality of scanning areas in the eye, and (b) an obtaining unit configured to obtain tomographic images corresponding to the number of times of scanning decided by said decision unit for each of the scanning areas, and
wherein said averaging unit adds and averages the tomographic images obtained by said obtaining unit for each of the scanning areas.

2. The apparatus according to claim 1, wherein said decision unit decides numbers of times of scanning with respect to the plurality of scanning areas to be smaller with increases in distance from a middle of the eye.

3. The apparatus according to claim 1, further comprising:
a calculation unit configured to calculate an S/N ratio representing a ratio between a signal level and a noise level with respect to each of the tomographic images obtained by said obtaining unit for each of the scanning areas; and
an extraction unit configured to extract tomographic images, of the tomographic images obtained by said obtaining unit for each of the scanning areas, which are added and averaged by said averaging unit, for each of the scanning areas based on the S/N ratio calculated by said calculation unit,
wherein said averaging unit adds and averages only the tomographic images, of the tomographic images obtained by said obtaining unit for each of the scanning areas, which are extracted by said extraction unit for each of the scanning areas.

4. The apparatus according to claim 3, wherein when the S/N ratio calculated by said calculation unit exceeds a predetermined value, said extraction unit extracts the tomographic images by a number smaller than when the S/N ratio is not more than the predetermined value.

5. The apparatus according to claim 1, wherein said averaging unit decreases the number of tomographic images to be used for averaging processing more with respect to each of the plurality of scanning areas with an increase in distance from a middle of the eye.

6. The apparatus according to claim 1, further comprising a calculation unit configured to calculate an S/N ratio representing a ratio between a signal level and a noise level with respect to each of the tomographic images obtained by said obtaining unit for each of the scanning areas,
wherein said decision unit decides the number of times of scanning by said scanning unit for each of the scanning areas based on the S/N ratio calculated by said calculation unit.

7. The apparatus according to claim 6, wherein when the S/N ratio calculated by said calculation unit exceeds a predetermined value, said decision unit decides a smaller number of times of scanning by said scanning unit than when the S/N ratio is not more than the predetermined value.

8. The apparatus according to claim 1, further comprising:
an illumination unit configured to illuminate the eye;
an imaging unit configured to image reflected light from the eye illuminated by said illumination unit to obtain an eye image; and
a calculation unit configured to calculate an S/N ratio representing a ratio between a signal amount and noise with respect to the eye image captured by said imaging unit,
wherein said decision unit decides the number of times of scanning by said scanning unit for each of the scanning areas based on the S/N ratio calculated by said calculation unit.

9. The apparatus according to claim 8, wherein when the S/N ratio calculated by said calculation unit exceeds a predetermined value, said decision unit decides a number of times of scanning by said scanning unit to be smaller than when the S/N ratio is not more than the predetermined value.

10. The apparatus according to claim 1, further comprising:
an illumination unit configured to illuminate the eye;
an imaging unit configured to image reflected light from the eye illuminated by said illumination unit to obtain an eye image; and
a detection unit configured to detect a lesion portion from the eye image captured by said imaging unit,
wherein said decision unit decides the number of times of scanning by said scanning unit for each of the scanning areas based on a position of the lesion portion detected by said detection unit.

11. The apparatus according to claim 10, wherein said decision unit decides a number of times of scanning by said scanning unit to be smaller in a scanning area corresponding to a position at which the lesion portion is not detected by said detection unit than in a scanning area corresponding to a position at which the lesion portion is detected.

12. A method of controlling an ophthalmic imaging apparatus which includes a scanning unit and a control unit, and obtains a tomographic image of an eye to be examined based on light obtained by combining (a) return light from the eye irradiated with measurement light with (b) reference light corresponding to the measurement light, the method comprising:
causing the scanning unit to scan the measurement light on the eye;
causing the control unit to control the number of times of scanning by the scanning unit in accordance with a scanning position of the scanning unit on the eye; and
adding and averaging tomographic images of the eye which are obtained at the scanning position,
wherein the scanning position includes positions of a plurality of scanning areas scanned by the scanning unit in the eye,
wherein the causing the control unit to control step comprises (a) deciding the number of times of scanning by the scanning unit with respect to each of the plurality of scanning areas based on the positions of the plurality of scanning areas in the eye, and (b) obtaining tomographic images corresponding to the number of times of scanning decided for each of the scanning areas, and wherein the adding and averaging step adds and averages the tomographic images obtained by the obtaining step for each of the scanning areas.

13. A non-transitory computer-readable storage medium storing a computer program for causing a computer to execute each step in a method of controlling an ophthalmic imaging apparatus defined in claim 12.

14. An ophthalmic imaging apparatus which obtains a tomographic image of an eye to be examined based on light obtained by combining (a) return light from the eye irradiated with measurement light with (b) reference light corresponding to the measurement light, the apparatus comprising:

a scanning unit configured to scan the measurement light on the eye;

a control unit configured to control the number of times of scanning by said scanning unit in accordance with a scanning position of said scanning unit on the eye; and an averaging unit configured to add and average tomographic images of the eye which are obtained at the scanning position, wherein the scanning position includes positions in a plurality of scanning areas scanned by said scanning unit in the eye, wherein said control unit comprises (a) an acceptance unit configured to accept input of the number of times of scanning by said scanning unit with respect to each of the plurality of scanning areas, and (b) an obtaining unit configured to obtain tomographic images corresponding to the number of times of scanning input by said acceptance unit for each of the scanning areas, and wherein said averaging unit adds and averages the tomographic images obtained by said obtaining unit for each of the scanning areas.

* * * * *